(12) United States Patent
Sabesan (10) Patent No.: US 11,033,220 B2
(45) Date of Patent: Jun. 15, 2021

(54) SYSTEMS AND METHODS OF LIMB-BASED ACCELEROMETER ASSESSMENTS OF NEUROLOGICAL DISORDERS

(71) Applicant: LivaNova USA, Inc., Houston, TX (US)

(72) Inventor: Shivkumar Sabesan, Houston, TX (US)

(73) Assignee: LivaNova USA, Inc., Houston, TX (US)

( * ) Notice: Subject to any disclaimer, the term of this patent is extended or adjusted under 35 U.S.C. 154(b) by 0 days.

(21) Appl. No.: 14/561,137

(22) Filed: Dec. 4, 2014

(65) Prior Publication Data

US 2015/0157252 A1 Jun. 11, 2015

Related U.S. Application Data

(60) Provisional application No. 61/912,511, filed on Dec. 5, 2013.

(51) Int. Cl.
*A61B 5/11* (2006.01)
*A61B 5/00* (2006.01)
*A61B 5/369* (2021.01)

(52) U.S. Cl.
CPC .............. *A61B 5/4094* (2013.01); *A61B 5/11* (2013.01); *A61B 5/369* (2021.01); *A61B 5/7221* (2013.01);
(Continued)

(58) Field of Classification Search
CPC ....... A61B 5/4094; A61B 5/11; A61B 5/1101; A61B 5/1104; A61B 5/1112;
(Continued)

(56) References Cited

U.S. PATENT DOCUMENTS

2008/0319281 A1* 12/2008 Aarts ................. A61B 5/02438
600/301
2009/0030345 A1* 1/2009 Bonnet ................. A61B 5/1116
600/587

(Continued)

OTHER PUBLICATIONS

Hildeman, Anders. "Classification of epileptic seizures using accelerometers." (2011).*

(Continued)

*Primary Examiner* — Christopher A Flory
*Assistant Examiner* — Nathan A Baldwin
(74) *Attorney, Agent, or Firm* — Foley & Lardner LLP (57) ABSTRACT

A method of detecting a subject's physiological status, seizure state, or seizure type with limb-based accelerometers identifying a favored accelerometer or limb that provides a better sensitivity or false positive rate as compared to other accelerometers or limbs. The detection method may include determining whether the seizure conforms with an anticipated seizure type, and determining whether to base a seizure detection on data from the favored or un-favored accelerometers or limbs. The method may also include applying a weighing factor to base the detection on data obtained primarily from the favored accelerometer or limb or to not rely on data obtained primarily from un-favored accelerometers or limbs. The method may also include comparing data obtained from a favored accelerometer or limb with data obtained from other accelerometers or limbs or obtained from detection devices using ECG or EEG. An alert may be generated based on the detection of a seizure.

17 Claims, 4 Drawing Sheets

(52) U.S. Cl.
CPC .......... *A61B 5/7246* (2013.01); *A61B 5/7282* (2013.01); *A61B 5/6824* (2013.01); *A61B 5/6828* (2013.01); *A61B 2562/04* (2013.01)

(58) Field of Classification Search
CPC .... A61B 5/1113; A61B 5/1114; A61B 5/1115; A61B 5/1116; A61B 5/1117; A61B 5/1118; A61B 5/112; A61B 5/1121; A61B 5/1122; A61B 5/1123; A61B 5/1124; A61B 5/1125; A61B 5/1126
See application file for complete search history.

(56) References Cited

U.S. PATENT DOCUMENTS

| | | | | |
|---|---|---|---|---|
| 2009/0062696 | A1* | 3/2009 | Nathan | A61B 5/1107 600/595 |
| 2010/0280335 | A1* | 11/2010 | Carlson | A61N 1/36082 600/301 |
| 2012/0296175 | A1* | 11/2012 | Poh | A61B 5/02405 600/301 |
| 2012/0310050 | A1* | 12/2012 | Osorio | A61B 5/4094 600/300 |
| 2013/0079602 | A1* | 3/2013 | Picard | A61B 5/0022 600/301 |
| 2013/0096391 | A1* | 4/2013 | Osorio | A61B 5/02055 600/301 |
| 2013/0281797 | A1 | 10/2013 | Sabesan | |
| 2014/0031635 | A1* | 1/2014 | Sabesan | A61B 5/7282 600/301 |
| 2014/0081090 | A1* | 3/2014 | Picard | G06F 19/3418 600/301 |
| 2014/0276129 | A1* | 9/2014 | Osorio | A61B 5/4094 600/483 |

OTHER PUBLICATIONS

Van de Vel, Anouk, et al. "Long-term home monitoring of hypermotor seizures by patient-worn accelerometers." Epilepsy & Behavior 26.1 (2013): 118-125.*
Shiffman, Daniel. The Nature of the Code. D. Shiffman, 2012, web.archive.org/web/20121102061902/https://natureofcode.com/book/chapter-10-neural-networks/.*
Azar, et al., Postictal breathing pattern distinguishes epileptic from nonepileptic convulsive seizures, Epilepsia, Jan. 2008, vol. 49, No. 1, 6 pages.
Bonnet, et al., A Magnetometer-Based Approach for Studying Human Movements, IEEE Transactions on Biomedical Engineering, Jul. 2007, vol. 54, No. 7, 3 pages.
Chapman, et al., Sudden Unexpected Death in Epilepsy: continuing the global conversation, Epilepsy Australia, Epilepsy Bereaved & Sudep Aware, Camberwell, Australia, 2011, 87 pages.
Cuppens, et al., Automatic video detection of body movement during sleep based on optical flow in pediatric patients with epilepsy, Medical & Biological Engineering & Computing, Sep. 2010, vol. 48, No. 9, 9 pages.
Cuppens, et al., Automatic Video Detection of Nocturnal Epileptic Movement Based on Motion Tracks, Proceedings of the International Conference on Bio-inspired Systems and Signal Processing (Biosignals-2012), Feb. 2012, 4 pages.
Cuppens, et al., Detection of Nocturnal Epileptic Seizures of Pediatric Patients Using Accelerometers: Preliminary Results, IEEE Benelux EMBS Symposium, Dec. 6-7, 2007, 4 pages.
Cuppens, et al., Detection of nocturnal frontal lobe seizures in pediatric patients by means of accelerometers: a first study, 31st Annual International Conference of the IEEE EMBS, Sep. 2-6, 2009, Minneapolis, Minnesota, 4 pages.
Cuppens, et al., Using Spatio-Temporal Interest Points (STIP) for myoclonic jerk detection in nocturnal video, 34th Annual International Conference of the IEEE EMBS, Aug. 28-Sep. 1, 2012, San Diego, CA, 4 pages.
Decaigny, et al., Accelerometers used for the detection of nocturnal frontal lobe seizures in pediatric patients, Proceedings of the European Conference on the Use of Modern Information and Communications Technologies, Jan. 25, 2010, 12 pages.
Loddenkemper, et al., Circadian patterns of pediatric seizures, Neurology, vol. 76, No. 2, Jan. 11, 2011, 9 pages.
Masse, et al., Miniaturized Wireless ECG-Monitor for Real-Time Detection of Epileptic Seizures, Wireless Health 2010, ACM, Oct. 5-7, 2010, San Diego, CA, 7 pages.
Osorio, et al., Extracerebral detection of seizures: A new era in epileptology?, Epilepsy & Behavior, Dec. 2011, vol. 22, 6 pages.
Remi, et al., Quantitative movement analysis differentiates focal seizures characterized by automatisms, Epilepsy & Behavior, Apr. 2011, vol. 20, No. 4, 6 pages.
Tinuper, et al., Movement disorders in sleep: Guidelines for differentiating epileptic from no-epileptic motor phenomena arising from sleep, Sleep Medicine Reviews, Aug. 2007, vol. 11, No. 4, 13 pages.
Van Looy, et al., Detection of body movement using optical flow and clustering, Proceedings of the 2nd International Conference on Positioning and Context-Awareness, Mar. 2011, retrieved from the Internet at http://scholar.googleusercontent.com/scholar?q=cache:v7u2PnmRjxMJ:scholar.google.com/&hl=en&as_sdt=0,44 on Apr. 13, 2016, 10 pages.

* cited by examiner

SYSTEMS AND METHODS OF LIMB-BASED ACCELEROMETER ASSESSMENTS OF NEUROLOGICAL DISORDERS

CROSS-REFERENCE TO RELATED APPLICATION

This application is a non-provisional application of U.S. Provisional Patent Application No. 61/912,511, filed Dec. 5, 2013. U.S. Provisional Patent Application No. 61/912,511 is hereby incorporated herein by reference in its entirety.

FIELD OF THE DISCLOSURE

The embodiments described herein relate to systems, devices, and associated methods for assessing neurological disorders such as, e.g. seizures relating to, among other things, epilepsy based, in part, on signals received from one or more accelerometers. More particularly, the embodiments described herein relate to devices, systems, and methods for detecting epileptic seizures based on signals received from an accelerometer placed on at least one limb of a patient.

BACKGROUND

Seizures are generally characterized by intermittent, abnormal/excessive neural activity in the brain. Seizures may involve loss of consciousness or awareness, and may cause falls, uncontrollable convulsions, etc. Significant injuries may result not only from the neuronal activity in the brain but also from the associated loss of motor function from falls or the inability to perceive and/or respond appropriately to potential danger or harm.

Epilepsy is a chronic disease characterized by seizures that may vary in frequency of occurrence and severity and may range from involving no impairment of consciousness at all to complete loss of consciousness. Typically, a seizure resolves within a few minutes and there is seldom need for any extraordinary medical intervention, other than maintaining the comfort and ensuring unobstructed breathing of the patient.

Various types of epileptic seizures exist, including generalized tonic clonic seizures (grand mal seizures) which are the most common and best-known type of generalized seizure. Tonic clonic seizures can begin with stiffening of the limbs (the tonic phase). The tonic phase is usually followed by jerking of the limbs and movement in the face (the clonic phase). Myoclonic seizures can be rapid, brief contractions of body muscles, which usually occur at the same time on both sides of the body. Occasionally, myoclonic seizures involve one arm or a foot. Atonic seizures (also referred to as astatic or akinetic seizures) can produce an abrupt loss of muscle tone and may result in head drops, loss of posture, and/or sudden collapse.

Another common type of epilepsy is frontal lobe epilepsy, or FLE. FLE has been characterized by brief, recurring seizures that arise in the frontal lobes of the brain. When compared to other types of seizures, such as generalized tonic clonic seizures, FLE seizures can often occur while the patient is sleeping, making detection difficult. The onset of an FLE seizure also may be difficult to detect since the frontal lobes contain and regulate many structures and functions and seizures occurring in these regions of the brain may produce unusual symptoms, which can often be misdiagnosed as a psychiatric disorder, non-epileptic seizure, or a sleep disorder. During the onset of a seizure, a patient may exhibit abnormal body posturing, sensorimotor tics, or other abnormalities in motor skills. Patients may be unaware that they are experiencing a seizure.

FLE seizure episodes that include complex hyperactivity of the proximal portions of the limbs that can lead to increased overall motor activity can be called hypermotor seizures. When associated with unregulated and unusual movements and vocalizations, these seizures are often misdiagnosed as pseudoseizures or other episodic movement disorders such as psychogenic movement disorders, familial paroxysmal dystonic choreoathetosis, paroxysmal kinesogenic choreoathetosis, or episodic ataxia. Hypermotor seizures in children may be sometimes confused with pavor nocturnus (night terrors).

In some cases, a seizure may lead to death. Asphyxia is an impairment or absence of the oxygen and carbon dioxide exchange in the body, which can occur, for example, during suffocation. Asphyxia has been considered the leading cause of Sudden Unexplained Death in Epilepsy Patients ("SUDEP") and may trigger SUDEP. SUDEP has been defined by some as death resulting from unexplained cardiac and/or respiratory failure following a seizure. However, the mechanism and relationship of SUDEP with cardiorespiratory and cerebral function has not yet been fully understood. SUDEP does not appear to occur during or, generally, immediately after an initial phase of a seizure but as the patient appears to be recovering from the seizure. In addition, SUDEP may occur at night, while the patient is sleeping. Such sudden unexplained death is not necessarily limited to seizure patients and may be underreported in the general population. Seizure patients, including those with epilepsy, seem to be at a higher risk for sudden unexplained death than the general population.

Some have described three phases relating to a typical seizure condition: ictal, post-ictal (or "postictal"), and inter-ictal. The ictal phase has been described as the initial portion of the seizure, where a patient may display symptoms, if any, such as convulsions. Generally speaking, the inter-ictal phase has been described as the period between seizures when the patient has substantially recovered.

It has been suggested that the post-ictal phase takes place immediately after the ictal phase of the seizure, where symptoms have subsided, but the patient has not yet returned to a normal and/or non-ictal state. During the post-ictal period, the patient may be relaxed or lying down and may appear to be sleeping. In the post-ictal period, the heart rate of a patient may typically take a few minutes to return to the non-seizure baseline of the patient. The same is true of the electrocardiogram ("EKG" or "ECG") measurements of the patient, if the patient should happen to be undergoing EKG testing at the time of the seizure. EKG measurements can provide a record of the integrated action of the heart over a period of time. Cardiac and respiratory readings for the patient may soon appear to be normal as the patient progresses in the post-ictal period. Such measurements and readings, along with visual observation, can support a view that a patient is coming out of the seizure in a normal fashion and is not at risk for SUDEP. One might thus conclude that no medical intervention is necessary. However, in some cases, such measurements, readings, and observations may be deceptive and leave the patient at risk of SUDEP. If a condition in a patient that leads to an increased risk of SUDEP can be detected, timely measures may be taken that can reduce that risk and possibly save the patient.

Therefore, it is important to reliably predict seizures prior to onset and/or to identify the initiation or occurrence of seizures as quickly as possible to allow therapeutic or responsive action to be taken, including the administration of a therapy, intervention to prevent injury to the patient, or the cessation of potentially-dangerous patient activities such as, e.g., operating a vehicle or climbing stairs. It is also important to be able to identify and record seizures that have occurred over time to accurately assess the state of the patient's condition and determine whether prior or ongoing therapies are effective or should be modified. Seizure detection and/or prediction algorithms have been proposed using a variety of body parameters to predict and detect seizures, including brain waves (e.g., electroencephalogram or EEG signals), and heartbeats (e.g., electrocardiogram or EKG signals).

Detection of seizures using heart data has involved the use of algorithms that distinguish between pathological changes in the detected heart signal (which indicate a seizure) and non-pathological changes that may be similar to pathological changes but involve normal physiological functioning. For example, the heart rate may rise both when a seizure event occurs and when the patient exercises, climbs stairs, or performs other physiologically demanding acts.

Seizure detection algorithms, in some instances, may need to distinguish between changes in heart rate due to a seizure and those due to exertional or positional/postural changes. As noted, it is important to detect seizures quickly and accurately. However, it is believed that current algorithms may not be reliable and may fail to provide rapid and accurate detection for at least some patients and in regard to some seizure types. It is also believed that current algorithms may also fail to provide an indication of when the seizure has ended and the danger to the patient is reduced in at least some patients and in regard to some seizure types.

It is believed that the effective management of epilepsy is enhanced by reliable long-term (over days and months) monitoring of seizures. Although, visual inspection of EEG signals and video surveillance as well as EEG are conventionally used to observe hypermotor seizures in supervised environments such as the epilepsy-monitoring unit or the intensive care unit of a hospital or other healthcare facility, it is not practical to use this approach to objectively quantify long-term seizure frequency. Conventional approaches to track long-term seizure frequency have involved the use of patient seizure diaries. However, it has been shown that self-reporting of seizure incidence may be inaccurate.

Therefore, a need exists for systems, devices, and methods for effective seizure detection via the detection of autonomic signatures such as motion signals that may be altered or otherwise affected by seizures.

SUMMARY

To address these and other unmet needs, the present disclosure provides, in exemplary non-limiting embodiments, systems, devices, and methods for effective seizure detection via the detection of autonomic signatures such as motor and/or cardiac signals that may be altered or otherwise affected by seizures. In particular, the present disclosure is directed to, among other things, wearable devices to chronically monitor cardiac or motor signals associated with seizures and monitoring, and the assessments thereof.

In at least one embodiment, described further below, methods of detecting a subject's physiological status or a seizure event are disclosure. At least some of these methods involve the placement of accelerometers on two or more limbs of the subject, and an evaluation of accelerometer and other data that determines which of the accelerometers or limbs is a better indicator of the subject's status or seizure state. The methods also can be used to identify a favored limb that is associated with a seizure or seizure type, and to identify limbs that are non-favored in the detection of seizures or seizure types. The methods are also useful in providing improved detection of seizures or types of seizures by facilitating the adjustment or calibration of seizure detection devices to improve the performance of such devices.

In one embodiment, a method of detecting a physiological status, seizure state, or seizure type of a subject is disclosed that includes the steps of coupling a plurality of accelerometers to the subject so as to dispose at least one accelerometer at each of at least two limbs of the subject, and identifying which of the plurality of accelerometers (or associated limb) provides better data regarding or a better indication of the subject's physiological status, the subject's seizure state, or the seizure type, with the better indication being defined by at least one of a greater level of sensitivity in a detection of the physiological status, seizure state, or seizure type and a lesser level of a false positive rate in the detection of the physiological status, seizure state, or seizure type. As can be appreciated, the accelerometer or limb identified as providing the better data or indication may be characterized as a favored accelerometer or limb, and that this characterization may also define un-favored accelerometers or limbs. As can be further appreciated, the physiological status may be a seizure status of the subject and, more specifically, the physiological status may be a hypermotor seizure status of the subject. The seizure type may also be a hypermotor seizure. The method may further include the step of identifying which of accelerometers or subject limbs is a favored in the detection or acquisition of data indicative of seizure type or hypermotor seizures, or in the determination of physiological status or seizure state of the subject. The method may further include the step of generating an alert in response to the detection of a seizure or seizure type, or to a change in the physiological status or seizure state of the subject, wherein the generation of the alert is based on data received from each of the plurality of accelerometers with a greater weight being assigned to the data associated with the favored accelerometer or limb, or with a lesser weight being assigned to the data associated with the un-favored accelerometers or limbs. The method may include the evaluation of only two or three limbs or may involve the evaluation of all of the subject's limbs, may be implemented at multiple places on the same limbs, and may be implemented during a monitored seizure condition of the subject. The method may also involve the comparison of the performance of each accelerometer to subject ECG or EEG data, and to additional accelerometer data obtained from the subject to identify which of the accelerometers or limbs is favored or un-favored in the detection of the physiological status, seizure event, or seizure type.

In another embodiment, a method of detecting a seizure or seizure status of a subject is disclosed that includes the steps of coupling a plurality of accelerometers to the subject so as to dispose at least one accelerometer at each limb of the subject, detecting a seizure event using ECG data acquired from the subject, EEG data acquired from the subject, and/or motion data acquired from at least one of the plurality of accelerometers; identifying which of the plurality of accelerometers provides data or values indicating a better sensitivity and/or a better false positive rate as compared to the other accelerometers during the detection of the seizure event, which may be defined as a favored limb or accelerometer and which may also identify un-favored limbs or accelerometers; and configuring a seizure detection system to detect subsequent seizure events by acquiring motion data from the limb that is associated with the accelerometer that provided the better sensitivity and/or the better false positive rate. The method may further include the step of configuring the seizure detection system to provide a greater weight in the detection of subsequent seizures to the motion data or values acquired from the favored limb or accelerometer, and/or to provide a lesser weight in the detection of subsequent seizures to the motion data or values acquired from the un-favored limbs or accelerometers. The method may also be used when the seizure event is a hypermotor seizure, and used when the seizure is a seizure type that is associated with SUDEP.

In yet another embodiment, a method of associating a limb of a subject with a seizure type is disclosed, with the method including the steps of disposing accelerometers at each limb of the subject or on a majority of the limbs of the subject and identifying a favored limb and un-favored limbs during a detection of a seizure event associated with the seizure type with a seizure detection system monitoring the subject and detecting the seizure event, with the favored limb being a limb that is associated with the acquisition of better data or providing a better sensitivity and/or a better false positive rate in the detection of the seizure type as compared to the un-favored limbs in the detection of the seizure type. As can be appreciated, the favored limb can also be associated with a particular seizure or a seizure type that is not classified or that possesses a characteristic that is partially indicative of a seizure type. The method may also include the step of configuring the seizure detection system to acquire motion data exclusively from the favored limb or to not acquire motion data from one or more un-favored limbs. The method may also include the step of configuring the seizure detection system to acquire motion data from the favored limb and at least one other source for data regarding the subject's seizure state, and further configuring the seizure detection system to provide a greater weighing factor to the motion data acquired from the favored limb as compared to the motion data acquired from the at least one other source. As can be appreciated, the at least one other source may be a device providing an EEG or ECG signal acquired from the subject, may be a video device, a thermal imaging system, a motion detector, a depth sensor, or an infrared laser device monitoring the subject, and may be an accelerometer coupled to the subject's torso or head.

In still another embodiment, a method of detecting a seizure in a subject is disclosed, with the method including the steps of detecting the seizure with a seizure detection system, with the seizure detection system acquiring motion data from a favored limb of the subject and from at least one other source and with the favored limb being a limb of the subject that is associated with better data or a better sensitivity and/or a better false positive rate in the detection of an anticipated seizure type as compared to the other limbs of the subject when the seizure detection system is configured to detect the anticipated seizure type from motion data acquired from the other limbs; determining whether the detected seizure conforms with the anticipated seizure type; and issuing an alert responsive to the detection of the seizure, with the issuance of the alert being based primarily on the motion data acquired from the favored limb when the detected seizure conforms with the anticipated seizure type and with the issuance of the alert being based primarily on the motion data acquired from the at least one other source when the detected seizure does not conform with the anticipated seizure type. The seizure or the anticipated seizure type may be a hypermotor seizure or a seizure or seizure type associated with SUDEP. The at least one other source may be a device providing an EEG or ECG signal acquired from the subject, may be a video device, a thermal imaging system, a motion detector, a depth sensor, or an infrared laser device monitoring the subject, and may be an accelerometer coupled to an un-favored limb of the subject or coupled to a torso or a head of the subject.

As can be appreciated, the aforementioned methods may be used to detect other types of seizures and seizure types in addition to hypermotor seizures, such as generalized tonic-clonic (GTC) seizures, tonic seizures, myoclonic seizures, clonic seizures, and infantile spasms that manifest as movements of the limbs and/or body, and combinations of the aforementioned types of seizures and spasms.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings.

DETAILED DESCRIPTION

The present disclosure is drawn to systems, devices, and associated methods for assessing seizures based in part on signals received from one or more accelerometers. More particularly, the embodiments described herein relate to devices, systems, and methods for detecting epileptic seizures based on signals received from an accelerometer placed on at least one limb of a patient. Those of ordinary skill in the art would understand that the accelerometers disclosed herein may be worn on any suitable location of the patient including, for example on a head of a patient or a tongue. That is, the accelerometer may be disposed on any body part subject to motion during a seizure.

As disclosed herein, the performance of seizure detection using wearable (e.g. limb-based) accelerometers in patients (e.g. pediatric patients ages 5-15 years) with hypermotor seizures was assessed. Time and frequency domain features were extracted from 3-dimensional (3-D) accelerometers placed on patients' limbs. A cross-validation approach was utilized to determine the optimal threshold for seizure detection. The seizure detection algorithm was run prospectively on the data using an embedded real-time implementation. Results from application of this algorithm to 7 patients (53 seizures) showed a high sensitivity (mean sensitivity: 97.02%) of seizure detection with a false positive rate of about 2.1 detections/hour. In some embodiments, as disclosed herein, the performance of seizure detection can be achieved via use of multi-modal sensors, placement of sensors in body locations other than the limbs, and patient-specific tuning of algorithm parameters over time.

Reference will now be made in detail to the exemplary embodiments of the disclosure, examples of which are illustrated in the accompanying drawings.

Hypermotor or hyperkinetic seizures are convulsive seizures with a frontal lobe onset. These seizures often may result in serious consequences such as injuries because of uncontrolled movements, dizziness and headache, and in some cases, may result in patient death. Accordingly, detection of hypermotor or hyperkinetic seizures is important.

As described above, hypermotor or hyperkinetic seizures may occur more commonly in the pediatric population than in adults. These seizures often occur at night when supervision and care is reduced. Challenges to detection of hypermotor seizures may occur, in part, because hypermotor seizures have subtle or no ictal patterns on the scalp EEG, and/or the resemblance of the clinical manifestations of hypermotor seizures to those of non-epileptic parasomnias make it very difficult to detect using clinical semiology. As disclosed herein, one novel solution to the above challenges is extra-cerebral detection of hypermotor seizures using accelerometers (ACMs). As can be appreciated, other devices may be used to provide signals or information concerning subject motion that are comparable to ACMs or that may compliment or enhance ACMs, such as a device providing an EEG signal, a device providing an ECG signal, a video device, a thermal imaging system, a motion detector, a depth sensor, an infrared laser device, and an accelerometer coupled to the subject's torso or head.

Figure 1:
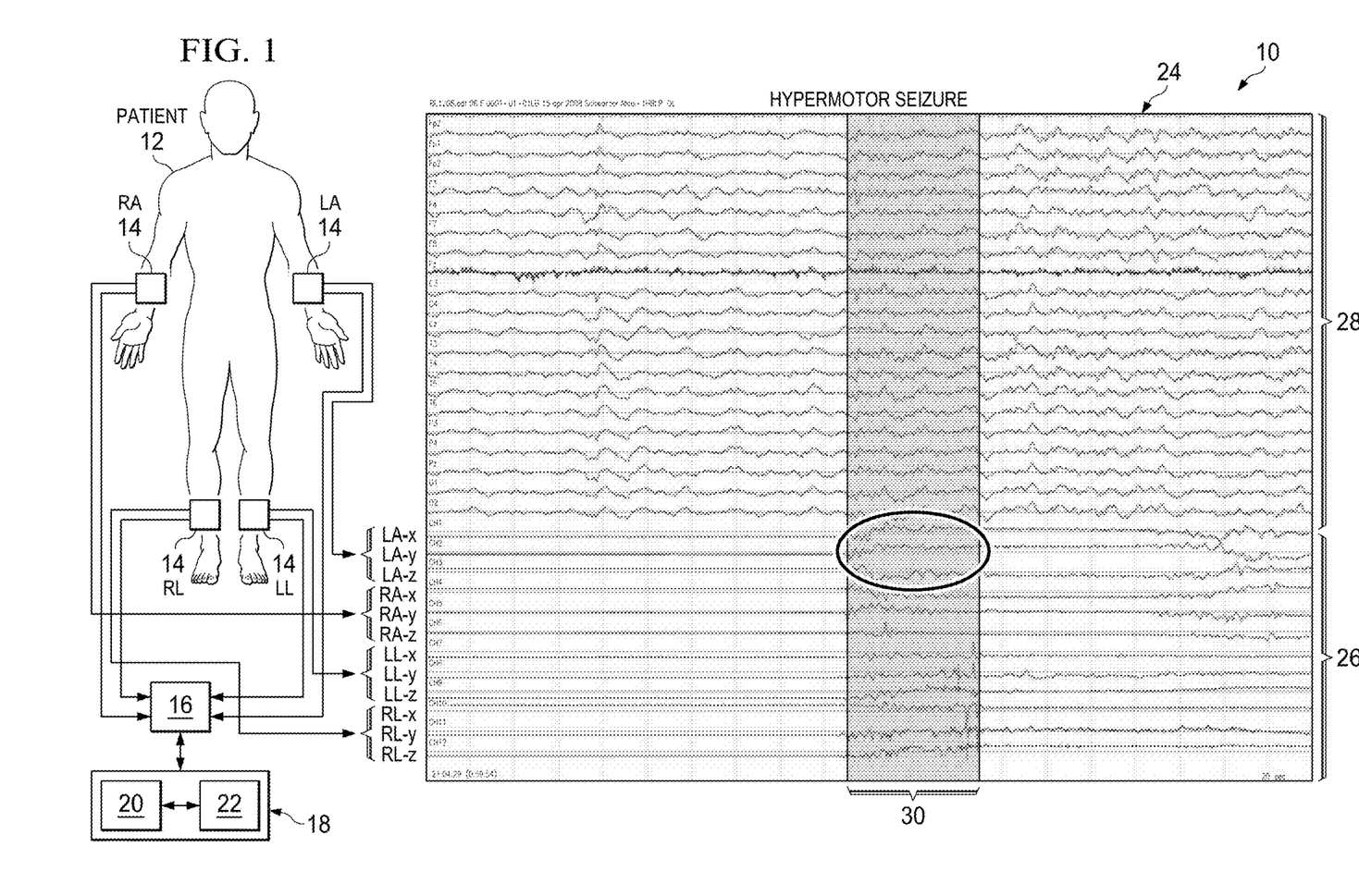
FIG. 1 is schematic illustration showing a graph acquired from simultaneous acquisition of video-EEG and a plurality of accelerometers during a hypermotor seizure, according to an exemplary embodiment of the present disclosure.

FIG. 1 shows a schematic system 10 of a patient 12 having four ACMs 14, each ACM 14 attached to a limb (e.g. an ACM 14 on the right leg (RL), the left leg (LL), right arm (RA), and left arm (RA)) In addition or alternatively, the ACMs 14 may be worn on any suitable body part including, head, chest, back, side of the torso, tongue, abdomen, etc. Each ACM 14 may send signals to a receiver 16, which may process the signals and/or send the processed signals to a system of servers 18 for further processing. The systems of servers 18 may include one or more servers, 20, 22, each of which may include a database of external data, such as the patient's medical history and/or medical history of other patient's having similar medical history profiles of the patient. The processed ACM data 26 may be displayed on a chart 24 along with EEG data 28 from the patient's scalp.

According to embodiments of the present disclosure, the one or more ACMs 14 may be placed on one or more limbs of a patient 12 to detect an autonomic signature. As used herein, the term autonomic signature refers to any medical event that may be detected, at least in part, by the ACM. Examples of such autonomic signature include, but are not limited to, hypermotor seizures, stroke, parkinsomnian tremors, and cardiac arrest. The chart 24 as shown in FIG. 1, graphs four ACM signals LA, RA, LL, and RL over time that are generated by three signals provided by each ACM (ACM-LA, ACM-RA, ACM-LL, and ACM-RL), with each ACM providing a signal for motion detected along each axis monitored by the respective ACM, i.e., LA (x-axis) at channel 1, LA (y-axis) at channel 2, LA (z-axis) at channel 3, RA (x-axis) at channel 4, RA (y-axis) at channel 5, RA (z-axis) at channel 6, LL (x-axis) at channel 7, LL (y-axis) at channel 8, LL (z-axis) at channel 9, RL (x-axis) at channel 10, RL (y-axis) at channel 11, and RL (z-axis) at channel 12.

The chart 24 of processed ACM data 26 may include a zone 30 indicating an autonomic signature, such as a hypermotor seizure.

Each ACM 14 may include any suitable sensor component configured to measure an inclination, a position, an orientation, and/or an acceleration of the patient in three dimensions. Such sensor components may include a piezoelectric component, a capacitive component, an electromechanical component, and/or any other sensing component.

The ACM 14 also may include a transmitter component configured to send the 3-D ACM sensor component data and/or other data to a receiver 16. The transmitter component of the ACM 14 may transmit signals detected by the ACM sensor to any suitable receiver 16 in any suitable manner, such as via wired communication or wireless communication. For example, the transmitter component of the ACM 14 may send signals wirelessly over a network, (not shown) such as the Internet, to one or more receivers 16. The receiver 16 may include one or more hardware components, such as memory and a processor for processing the signals.

The receiver 16 also may include a data communication interface for packet data communication and a central processing unit (CPU), in the form of one or more processors, for executing program instructions, such as programs for analyzing permittivity data. These components also may include an internal communication bus, program storage, and data storage for various data files to be processed and/or communicated by the receiver 16 such as ROM and RAM, although the ACM transmitters, and the receiver 16, also may receive programming and data via network communications. The hardware elements, operating systems, and programming languages of the ACM 14, and receiver 16, may be conventional in nature, and it is presumed that those skilled in the art are adequately familiar therewith. The receiver 16 also may include input and output ports to connect with input and output devices such as keyboards, mice, touchscreens, monitors, displays, etc. Of course, the various functions may be implemented in a distributed fashion on a number of similar platforms, to distribute the processing load.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of a communication network onto the computer platform of a server and/or from a server to the receiver 16. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

In some embodiments, the ACM 14 may include locational detection components, such as GPS components to detect the location of the ACM 14. In some embodiments, the ACM 14 may include an alert component, such as an audio alarm, vibrating alarm, and/or an optical alarm (e.g. flashing light) to alert the patient 12 and/or caregiver of an autonomic event, such as a hypermotor seizure. In some embodiments, the alert may be sent to a remote healthcare provider, and/or emergency services dispatcher at one or more remote locations. In some embodiments, one or more ACMs 14 may be in communication with each other to validate signal detection.

The ACM 14 may be placed directly or indirectly on any suitable location on a patient, including a limb of a patient. For example, the ACM 14 may be placed on the wrist, ankle, knee, elbow, fingers, toes, shin, etc. The ACM 14 may be placed on a limb in any suitable manner. For example, the ACM 14 may include a strap, band, patch clip, pouch, a garment, hook, belt, VELCRO™, elastic, pins, adhesive, glue, etc., to removably attach the ACM 14 to the patient's limb, either directly on the skin of the patient or on clothing worn by the patient 12. The ACM 14 may directly contact the patient's skin with fixation of the ACM 14 to the patient provided by tape extending over the ACM 14 or by an adhesive disposed between the ACM 14 and the patient. The ACM 14 may also indirectly contact the patient via an intermediary interface, such as with an ACM 14 mounted on one side of an adhesive label with an opposing side of the adhesive label engaging the patient's skin with an adhesive, or with an ACM 14 mounted on an item of clothing that is worn by the patient such as a band, a bracelet, or a ring, or with the ACM 14 embedded within clothing such as children's sleepwear. In some embodiments, the ACM 14 may be implanted beneath the skin of the patient, or one or more ACMs 14 may be implanted while other AMCs 14 are disposed external to the patient. The ACM 14 may have various properties, such as therapeutic drug delivery properties, (e.g. transdermal patch), etc. In some embodiments, multiple ACMs 14 may be placed on a limb at the same location or at different distances along the length of the limb such as, for example, at the wrist and at the elbow or at the ankle and at the knee. As can be appreciated, the ACM 14 can be placed in a position on the limb that corresponds to a joint, a muscle, or a muscle group, or at a position on the limb where a seizure-related movement is expected to be more pronounced.

The ACM 14 may be housed in any suitable housing having any suitable size, shape, and geometry. For example, the ACM 14 may be housed in an electronic device, such as a phone, an electronic music player, pedometer, watch, bracelet, wristband, etc. The ACM housing also may include other components that may be connected to the ACM 14, such as one or more input components (e.g. keyboard, touchscreen, mouse, buttons, etc.), and/or output components (e.g. displays, printers, etc.)

The chart 24 shown in FIG. 1 illustrates an example of a simultaneous acquisition of video-EEG and 12 channels of ACMs during a hypermotor seizure. In this example, four 3-D ACMs 14 were used. Each ACM 14 was placed on one of the left arm (LA), right arm (RA), left leg (LL), and right leg (RL), respectively, to generate 12 channels of motion signals with each ACM 14 providing data regarding the x, y, and z axis. A zone of detection 30 marks the onset of an autonomic signature, such as a hypermotor seizure. It was found no measurable change could be observed on the scalp EEG as zone 30. However, onset of a hypermotor seizure was observed on the ACM channels at zone 30.

The results of the data collected using the acquisition method shown in FIG. 1 and described above is shown in Table 1 below:

TABLE 1

| Patient No. | Age (years) | Number of Seizures | Length of Recording (hours) |
|---|---|---|---|
| 1 | 7.6 | 28 | 70.7 |
| 2 | 6.5 | 4 | 88.8 |
| 3 | 15.2 | 3 | 22.6 |
| 4 | 5.4 | 2 | 264.5 |
| 5 | 9.9 | 14 | 81.5 |
| 6 | 10.3 | 2 | 11.9 |
| Mean Age: 9.1 | | Total seizures: 53 | Total length: 540 |

The data was collected at the Epilepsy Centre for Children and Youth, Pulderbos, Belgium under the study protocol IWT-TBM 070713. Informed consent was obtained from patients/caregivers and the data was de-identified prior to transfer for analysis. A seizure detection algorithm was run using data from each 3-D ACM 14 placed in LA, RA, LL and RL location separately as well as taking all the ACM data from all limbs together. Table 1 shows that a total of 53 seizures were detected over a total ACM recording time of 540 hours.

Figure 2:
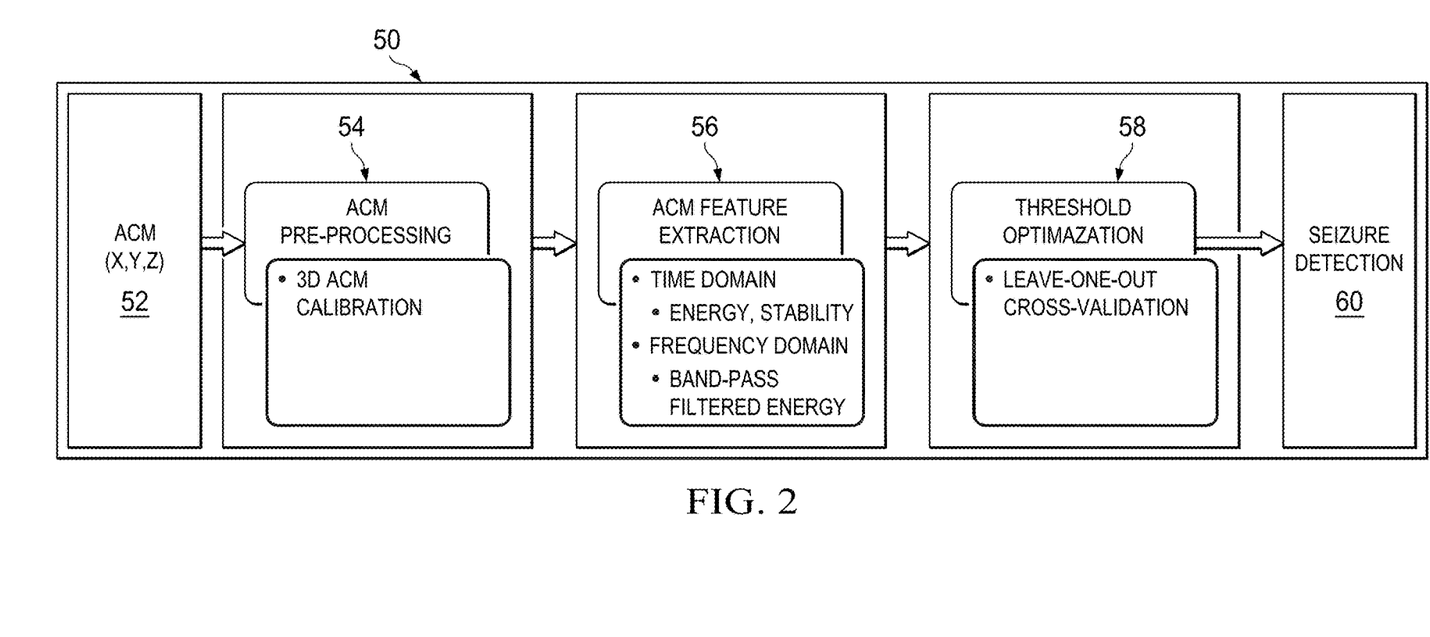
FIG. 2 is a block flow diagram showing a seizure detection algorithm, according to another exemplary embodiment of the present disclosure.

FIG. 2 shows an example of a seizure detection framework 50 using 3-D ACM signals. The raw ACM data (ACM (X, Y, Z)) 52 was calibrated at step 54 and provided to a feature extraction block at step 56 from which time and frequency domain features were extracted. The seizure detection thresholds on these features were determined using a leave-one-out cross-validation technique at step 58 following which the seizure detection decision is made at step 60.

As shown in FIG. 2, the seizure detection framework 50 involves initial calibration of the accelerometer at step 54 followed by feature extraction at step 56, threshold optimization at step 58, and seizure detection at step 60. The first step, ACMs processing at step 54, includes 3-D calibration of the ACMs 14. During the calibration step 54, the one or more ACMs 14 may be calibrated to define the orientation and other baselines for the ACMs 14. The calibration may be achieved in any suitable manner. For example, ACMs 14 may be placed on each limb of the patient 12 while the patient lies down prior to going to sleep at night. Each ACM 14 may then be set to a baseline threshold just prior to the patient falling asleep with, for example, the movement and acceleration of movement of each ACM 14 in each dimension set to zero.

The step of ACM feature extraction at step 56 includes various measurement domains, such as time, energy stability, frequency, and band-pass filtered energy. The time domain may measure the duration of the detected autonomic signature using, for example, the duration of a hypermotor seizure. The frequency domain may measure how often the autonomic signature occurs.

In addition, the band-pass filtered energy domain, when used, may use various factors in an algorithm to calculate a measure of the amount of energy expended. Examples of such various factors include: the coordination of patient movement during the autonomic signature, the intensity of the movement, the amount of energy expended by the patient during the autonomic signature, and the rhythmicity, coordination, and/or other characteristics of the patient during the autonomic signature in each of three dimensions.

The threshold optimization step at stop 58 may include various statistical algorithms and methods to determine optimal thresholds for one or more of the factors and/or characteristics identified in the ACM feature extraction step 56. Examples of such statistical methods may include leave-one-out cross-validation, nearest neighbor cross-validation, etc.

Figure 3:
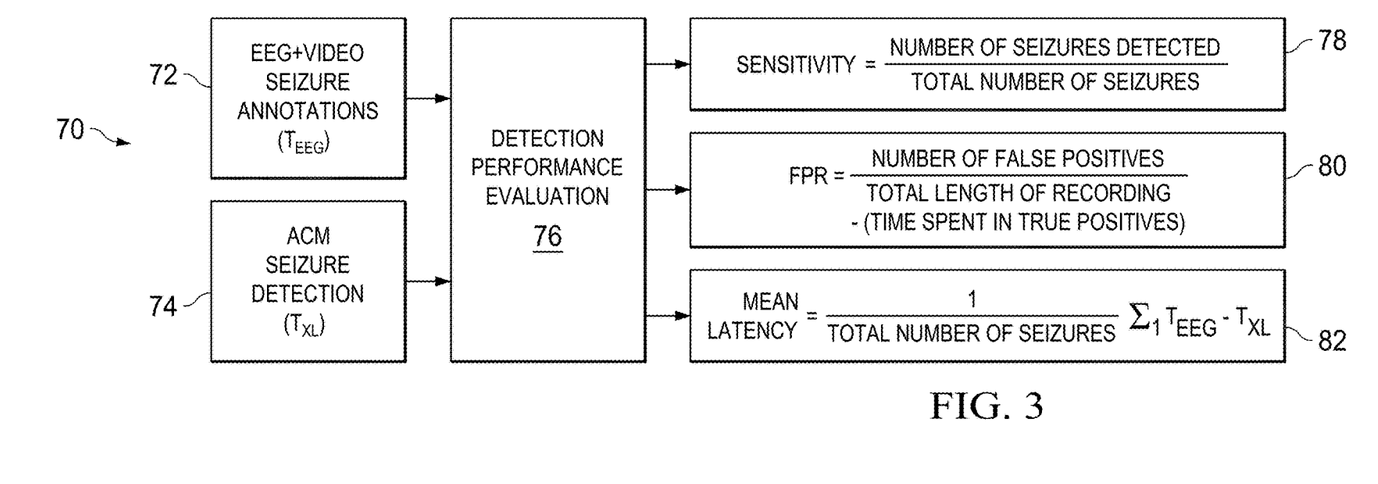
FIG. 3 is a flow diagram showing a seizure detect performance algorithm, according to another exemplary embodiment of the present disclosure.

FIG. 3 shows an example of a seizure detection performance evaluation 70. In this example, EEG+video Seizure Annotations ($T_{EEG}$) 72 are used to assess ACM seizure detection ($T_{XL}$) data 74 in a detection performance evaluation at step 76. Various statistical analysis algorithms are used to assess the ACM data, including calculating sensitivity 78 of the ACM seizure detection:

$$\text{Sensitivity} = \frac{\text{\# Seizures Detected}}{\text{Total \# of Seizures}},$$

calculating false positive recordings (FPR) 80:

$$FPR = \frac{\text{\# False Positives}}{\text{Total length of recording} - \text{(time spent in true positives)}}.$$

and calculating mean latency 82:

$$\text{Mean Latency} = \frac{1}{\text{Total \# of seizures}} \sum_1 TEEG - TXL.$$

Figure 4:
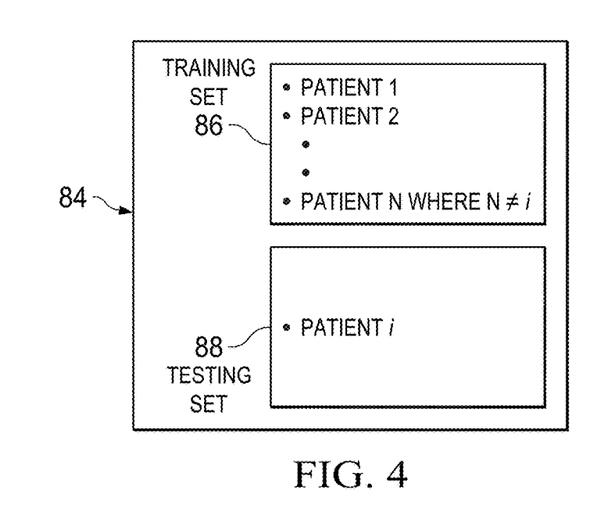
FIG. 4 is a diagram illustrating a seizure detection threshold optimization method, according to another exemplary embodiment of the present disclosure.

With reference to FIG. 4, a training set 86 of N patients, where N was not equal to i, is used and compared to a testing set 88 of i patients. A detection window of ±2 minutes from the annotated seizure onset is used to determine True and False Positive detections. As shown in FIG. 4, a cross-validation technique may be used to determine a seizure detection threshold. In the example illustrated in FIG. 4, a leave-one-out cross-validation technique 84 is used to evaluate training set 86 and testing set 88. However, any other suitable cross-validation technique may be used in addition to or as an alternative to leave-one-out cross-validation. Such cross-validation techniques include, but are not limited to nearest neighbor, k-fold, 2-fold, and repeated random sub-sampling. For each patient i, the seizure detection threshold may be determined using the data from all the other patients by minimizing the function $\sqrt{(1-\text{sensitivity})^2 + FPR^2}$. The obtained threshold then may be used to run the algorithm on Patient i. This process may be repeated for every patient and the sensitivity, FPR, and latency may be determined. The seizure detection algorithm may be optimized for computational and power efficiency for implementation on a suitable processor, such as the TI-MSP430 processor. The seizure detection algorithm may be run prospectively in real-time to detect seizures.

Figure 5:
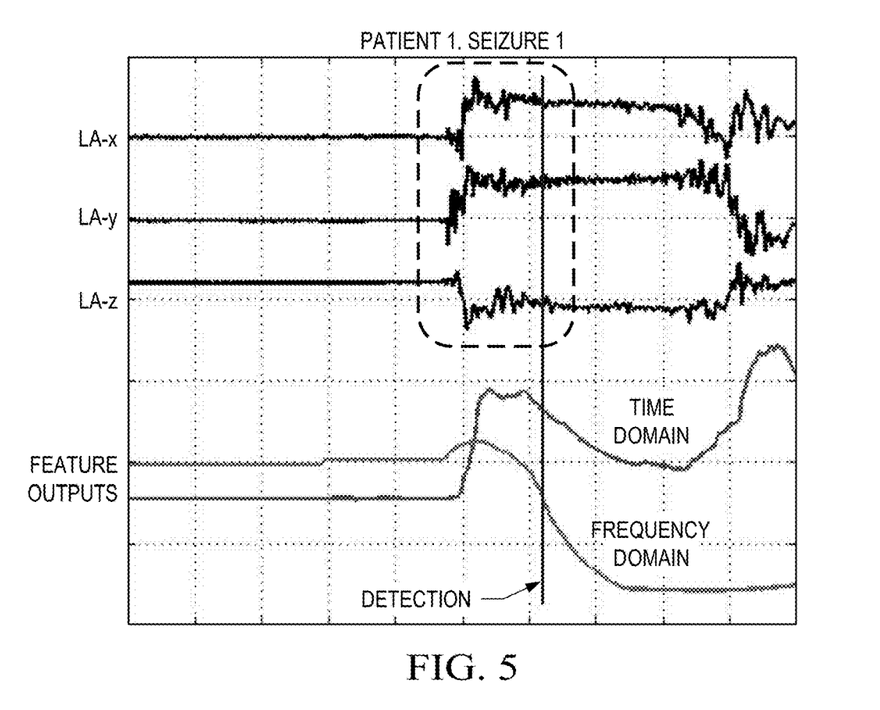
FIG. 5 is a graph illustrating the results of seizure detection performance in a first patient, according to another exemplary embodiment of the present disclosure.
Figure 6:
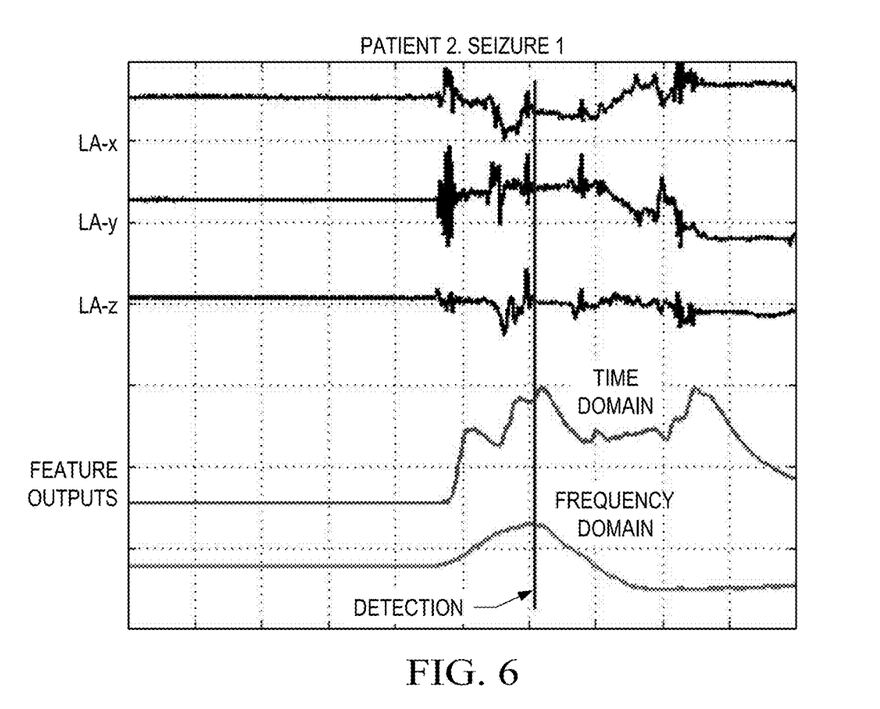
FIG. 6 is a graph illustrating the results of seizure detection performance in a second patient, according to another exemplary embodiment of the present disclosure.

FIGS. 5 and 6 show the results of the seizure detection performance of seizure detection technique using 3-D ACMs 14 such as those illustrated in FIG. 1. FIGS. 5 and 6 show examples of seizure detection outputs from two hypermotor seizures experiences by two patients, Patient 1 and Patient 2. FIG. 5 shows a detection output for a seizure (shown as a vertical line) for Patient 1 which is the same patient depicted in the signals illustrated in FIG. 1. FIG. 6 shows a detection output for another seizure (shown as a vertical line) for Patient 2. As shown in FIG. 5, the 3-D ACM signal associated with the left arm of Patient 1 indicates the detection of a hypermotor seizure having a peak duration and high frequency and a sustained short duration of subsequent peaks at a steady frequency, followed by another peak followed by a sustained short duration of peaks at a steady frequency. In contrast, FIG. 6 shows a 3-D ACM signal associated with the left arm of Patient 2 indicating a detection of a hypermotor seizure characterized by a cluster of peaks at a high frequency and having a relatively short duration. FIGS. 5 and 6 together show that although autonomic events may have different characteristics in different patients or at different times, the ACMs 14 achieve detection of the autonomic events in different patients.

Table 2 below summarizes the results of the seizure detection performance evaluation for a single 3-D ACM 14 on the left arm of six patients (Patients Nos. 1-6).

TABLE 2

| Pt. No. | No. of Seizures | Duration (hours) | Sensitivity (Se) (%) | FPR (/hr) | Latency (seconds) |
|---|---|---|---|---|---|
| 1 | 28 | 70.7 | 82.14 | 2.44 | 2.6 ± 0.5 |
| 2 | 4 | 88.8 | 100 | 2.36 | 2.8 ± 0.5 |
| 3 | 3 | 22.6 | 100 | 1.94 | 3.6 ± 0.7 |
| 4 | 2 | 264.5 | 100 | 2.55 | 3.2 ± 1.1 |
| 5 | 14 | 81.5 | 100 | 2.61 | 3.1 ± 1.7 |
| 6 | 2 | 11.9 | 100 | 0.91 | 1.8 ± 1.2 |
| Total seizures: 53 | Total length: 540 | Mean Se: 97.02 | Mean FPR: 2.13 | Mean latency: 2.85 ± 0.95 | |

The results summarized in Table 2 show that a total of 53 seizures were detected over a total of 540 hours. The sensitivity of the seizure detection by the ACM 14 on the left arm of the patients is calculated as described above, and it was determined that the detection had a mean sensitivity of about 97.02%. In other words, the left arm ACM 14 was accurate in detecting seizures 97.02 of the time. The false positive rate (FPR) per hour was also calculated, as described above, and it was determined that the mean FPR per hour was about 2.13 false detections per hour. The latency (e.g. how quickly an autonomic event was detected) was also calculated and it was determined that the mean latency was about 2.85 seconds±0.95 seconds.

Table 3 below summarizes the results of the seizure detection performance evaluation using a combination of 3-D ACMs on all limbs of a patient (LA, RA, LL, and RL).

TABLE 3

| Pt. No. | No. of Seizures | Duration (hours) | Sensitivity (Se) (%) | FPR (/hr) | Latency (seconds) |
|---|---|---|---|---|---|
| 1 | 28 | 70.7 | 82.14 | 2.64 | 2.6 ± 0.5 |
| 2 | 4 | 88.8 | 100 | 2.66 | 2.8 ± 0.5 |
| 3 | 3 | 22.6 | 100 | 3.24 | 3.6 ± 0.7 |
| 4 | 2 | 264.5 | 100 | 2.95 | 3.2 ± 1.1 |
| 5 | 14 | 81.5 | 100 | 2.91 | 3.1 ± 1.7 |
| 6 | 2 | 11.9 | 100 | 1.97 | 1.8 ± 1.2 |
| Total seizures: 53 | Total length: 540 | Mean Se: 97.02 | Mean FPR: 2.72 | Mean latency: 2.85 ± 0.95 | |

As shown in Tables 2 and 3 above, the results obtained from a prospective analysis of the limb-based 3-D ACMs 14 data appear to be comparable with respect to false positive rate than conventional methods that may, for example, rely mostly on EEG data. This may be primarily because most of the results reported using conventional methods (i.e. using solely cerebral detection) have been produced using retrospective analysis of data that utilized a classification scheme to classify ictal events from non-ictal events in a limited and pre-selected amount of data. The present algorithm was prospectively run in real-time to detect seizures.

As shown in Tables 2 and 3, the performance of real-time, prospective seizure detection using limb-based accelerometers appears to have high sensitivity (mean Se: 97.02%) of detecting hypermotor seizures. The mean latency of seizure detection across all patients was 2.85±0.95 seconds. Such short latencies to detect convulsive seizures are critical to aid in fast response.

Tables 2 and 3 indicate that placement of ACMs 14 on one of more limbs is attractive from a wearability standpoint, particularly because the skeletal structure of the limb has high degrees of freedom and is implicated in several physiological movements during sleep. In addition, the performance of seizure detection using this approach may be highly sensitive. Furthermore, the motion data (obtained from ACMs 14 mounted on one or more limbs) collected during a seizure event can be used to identify the limb or limbs (or other body part) that exhibit the greatest or most detectable motion indicative of the seizure event and/or the type of seizure event, i.e., a favored limb. The identification of a favored limb that relates to a seizure event or seizure type for a particular patient allows the patient or the health care provider to thereafter mount the ACM 14 on the favored limb for the anticipated seizure type and obtain improved data that is not obtainable or that is less obtainable when the ACM 14 is mounted on another limb of the patient (a limb that is less involved with the anticipated seizure type). The identification of a favored limb (or ACM 14 position on the body) can also be used to evaluate ACMs located elsewhere on the body to rule out false positives generated by those other ACMs. For example, a potential seizure detected on a non-favored limb could be further evaluated by inquiring whether the ACM 14 on the favored limb reported motion indicative of a seizure, with the value of the non-favored ACM data being weighed by the favored ACM data to rule out a false positive generated by the non-favored ACM, or to lead to further processing of the data received from both ACMs to better characterized whether the detected motion is a seizure event. Still furthermore, by having a favored limb associated with a particular seizure type, the detection of a seizure type can be used to determine whether the ACM on the favored limb should have greater influence on the reporting of a seizure event by the processor receiving the data from multiple AMCs. For example, when a known seizure type (associated with a favored limb) is detected at the ACM on a favored limb, the processor can provide greater weight to the data from the favored ACM when determining whether the detected motion qualifies as a reportable seizure event in view of seizure data obtain via other ACMs or other seizure detection systems. In contrast, when an unknown or unclassified seizure type is detected at the ACM on a favored limb, the processor can use the unclassified status of the potential seizure motion to eliminate the weighing normally given to the favored ACM and weight each ACM equally or according to a different protocol because the detected motion is not reliably associated with the favored limb. The aforementioned signal processing techniques and ACM arrangements can be used to improve the detection of seizures associated with limbs or other body parts, and can be used to reduce false positives by eliminating or reducing the influence of ACMs associated with limbs or body positions that are not demonstrably associated with a known seizure or seizure type.

High Sensitivity and Specificity of seizure detection algorithms is critical for long-term monitoring in an at-home setting, especially, during nighttime. To aid in this endeavor, in some embodiments, multimodal seizure detection using additional autonomic signatures associated with seizures such as EKG and respiration may be used.

In some embodiments, data from each ACM 14 placed on the limbs of the patient 12 may be analyzed to determine whether the movement of certain limbs is specific to certain different types of seizures. This data may be used to optimize algorithms and to allow signals from the ACMs on other limbs to be filtered out. The data may also be used to improve the false positive rate (FPR) by eliminating, weighing, or further processing data received from ACMs 14 that are placed on limbs that are not specific to the detected seizure, or by requiring confirmation or correlating data from the ACM 14 that is placed on a limb that is specific to the detected seizure. For example, it may be found that in one patient that hypermotor seizures are best detected by signals sent by an ACM 14 on the right leg, whereas another autonomic signature is best detected by signals sent by an ACM 14 on the left arm of the patient. In this example, signals from ACMs 14 other than the ACM 14 on the right leg may be filtered out or weighed in order to detect a hypermotor seizure in the patient, or the ACMs 14 on the other limbs may be discounted or subject to confirmation based on the data received from the ACM 14 on the right leg. Furthermore, in this example, the data from the ACMs 14 on the right leg or on the other limbs may be weighed or compared with each other in a context provided by the type of seizure detected by the ACMs, so that the right-leg ACM 14 has greater influence on seizure detection when a right-leg associated seizure is detected but have diminished or co-equal influence with the other ACMs 14 when the detected seizure is determined to be another type of seizure that has not been associated with the right-leg ACM 14.

In some embodiments, data from a video or visual monitoring device, such as a video camera, a Kinect sensor, an RF motion detector, or a depth sensor, can be used to determine the optimal placement of ACM 14 on the patient 12. This visual-driven placement of ACMs 14 can enrich the data to contain signals from only those body locations that may get implicated in a seizure or seizure type and thus help to optimize algorithms.

In some embodiments, it may be determined, using an ACM 14 and other patient diagnostic data, that movement of specific limbs of a patient 12 are associated with specific portions of the patient's brain, heart, or other organs, or with specific disease states, asphyxia, or SUDEP. Based on this data, therapeutic methods may be optimized for the patient 12 and diseases or autonomic signatures in other organs, such as a heart attack, may be predicted and/or detected. Likewise, alerts or therapies can be provided in response to the detection of movements that may be epileptic, asphyxia, SUDEP-related, or otherwise dangerous to the patient.

In some embodiments, one or more ACMs 14 may be placed on the limbs of patients with Parkinson's disease or other neurological diseases. The ACM data may be continuously monitored over time and analyzed to assess the effectiveness of various drugs and other therapies the patient 12 may be receiving. The type, amount, frequency, or cessation of a therapy may be determined based on this feedback loop of patient ACM data.

In some embodiments, ACM data may be analyzed to predict an autonomic signature, such as a hypermotor seizure. For example, if the patient has a history of cluster seizures (e.g. multiple discrete seizures in succession), ACM data identifying the onset of a first hypermotor seizure may alert the patient 12 and/or caregivers of the beginning of a cluster seizure and may allow time and preparation for ensuring treatment and/or safety of the patient 12.

In some embodiments, the ACM 14 may be worn externally on a limb, in any suitable manner, such as on a wristband, ankle band, and patch. In other embodiments, the ACM may be worn on the neck (e.g. a neck brace), in the mouth (e.g. tongue clip and/or ring, dental implant), etc.

In some embodiments, signals from an ACM 14 placed on a limb indicating a hypermotor seizure may be analyzed and correlated with the occurrence of one or more other autonomic events in the same patient or other patients having similar medical histories and/or similar demographic profiles. For example, in the past, certain signals from an ACM 14 placed on a patient's right arm indicating a hypermotor seizure may have preceded a heart attack in the patient by 3 days. Subsequent similar signals from the ACM 14 placed on the patient's right arm, may be processed, and used as a predictor of a subsequent heart attack in the patient.

In some embodiments, the ACM 14 may include other diagnostic sensors, such as cardiac sensors using any suitable technology, such as optical sensors. For example, the ACM 14 may be placed on the neck around the carotid artery or jugular vein, on the wrist near the radial artery, on the inside of the elbow near the brachial artery, behind the knee near the popliteal artery, on the ankle near the posterior or tibial artery, and/or on the foot neat the dorsalis pedis artery. The ACM 14 placed on these locations may detect body movement as well as measure cardiac data.

In some embodiments, the ACMs may be placed in locations on or in the body other than the limbs.

In some embodiment, the patient and/or caregiver may adjust the autonomic signature detection threshold settings, chronically over time so as improve the patient customized performance of the autonomic signature detection in an at-home setting.

What is claimed is:

1. A method of detecting a seizure status of a subject, the method comprising:
   collecting data from a first accelerometer coupled to a first limb of the subject and a second accelerometer coupled to a second limb of the subject;
   determining, via a processor, that the first accelerometer provides a better indication of the seizure status of the subject as compared to the second accelerometer based on the data collected from the first accelerometer and the second accelerometer, the better indication defined by at least one of a greater level of sensitivity in a detection of the seizure status than provided by the second accelerometer or a lesser level of a false positive rate in the detection of the seizure status than provided by the second accelerometer;
   detecting an indication of the seizure status of the subject using the data collected from the first accelerometer or the second accelerometer; and
   generating an alert in response to the detection of the indication of the seizure status of the subject, wherein generating the alert comprises a determination to report the alert based on the data collected from the first accelerometer and the second accelerometer with a greater weight assigned to the data associated with the first accelerometer, wherein in response to determining the data associated with the second accelerometer indicates a potential physiological event, weighting a value of the data associated with the second accelerometer by the data associated with the first accelerometer to confirm the indication of the seizure status.

2. The method of claim 1, wherein the seizure status is a hypermotor seizure status of the subject.

3. The method of claim 1 further comprising:
   identifying which of the at least two limbs is associated with the better indication of the seizure status of the subject.

4. The method of claim 3 wherein the seizure status is a hypermotor seizure status of the subject.

5. The method of claim 1 wherein determining, via the processor, that the first accelerometer provides the better indication of the seizure status of the subject includes associating each accelerometer with the limb of the subject to which the accelerometer is coupled and evaluating a performance of each accelerometer during an annotated seizure condition of the subject.

6. The method of claim 5 wherein determining, via the processor, that the first accelerometer provides the better indication of the seizure status of the subject further includes comparing the performance of each accelerometer to at least one of ECG data acquired from the subject, EEG data acquired from the subject, or motion data acquired from at least one accelerometer.

7. The method of claim 6, wherein the at least one of the greater level of sensitivity or the lesser level of the false positive rate is determined based on comparing the performance of each accelerometer to a detected seizure condition of the at least one of ECG data acquired from the subject, EEG data acquired from the subject, or motion data acquired from at least one accelerometer.

8. The method of claim 5, wherein the at least one of the greater level of sensitivity or the lesser level of the false positive rate is determined based on comparing the annotated seizure condition to the performance of each accelerometer in detecting the seizure state.

9. A method of detecting a seizure status of a subject, the method comprising:
   collecting motion data from a first accelerometer coupled to a first limb of the subject and a second accelerometer coupled to a second limb of the subject;
   detecting, via a processor, a first type of seizure event using at least one of ECG data acquired from the subject, EEG data acquired from the subject, or the motion data collected from at least one of the first accelerometer or the second accelerometer;
   determining, via the processor, that the first accelerometer provides a better sensitivity and/or a better false positive rate than the second accelerometer in the detection of the first type of seizure event based on the motion data collected from the first accelerometer and the second accelerometer; and
   configuring a seizure detection system to:
      detect a type of seizure event in subsequent seizures;
      responsive to the type of seizure event being the first type of seizure event, provide a greater weight to the motion data from the limb associated with the first accelerometer that provides the better sensitivity and/or the better false positive rate, wherein the greater weight is greater than a first weight applied to the second accelerometer in the detection of the first type of seizure event; and responsive to the type of seizure event being a second type of seizure event, provide a lesser weight to the motion data from the limb associated with the first accelerometer, wherein the lesser weight is less than a second weight applied to the second accelerometer in the detection of the first type of seizure event, wherein the second accelerometer provides a better sensitivity and/or a better false positive rate than the first accelerometer for the second type of seizure event;

wherein the provided weights are used to confirm detection of the subsequent seizure events.

10. The method of claim 9 further comprising:
configuring the seizure detection system to provide a lesser weight in the detection of subsequent seizures to motion data from one or more limbs that are not associated with the first accelerometer that provides the better sensitivity and/or the better false positive rate in the detection of subsequent seizures of the first type of seizure event.

11. The method of claim 9 wherein the seizure event is at least one of a hypermotor seizure or a seizure type associated with Sudden Unexplained Death in Epilepsy Patients ("SUDEP").

12. A method of associating a limb of a subject with a seizure type, the method comprising:
disposing accelerometers at each limb of the subject;
identifying, via a seizure detection system comprising a processor, a favored limb and un-favored limbs in a detection of the seizure type with the seizure detection system monitoring the subject, the favored limb being a limb that is associated with a better sensitivity and/or a better false positive rate in the detection of the seizure type as compared to the un-favored limbs in the detection of the seizure type;
configuring the seizure detection system to acquire motion data from the accelerometer disposed on the favored limb and at least one other source; and
further configuring the seizure detection system to:
in response to the motion data acquired from at least one of the accelerometer disposed on the favored limb or the at least one other source indicating a potential physiological event corresponding to the seizure type, provide a greater weighing factor to the motion data acquired from the accelerometer disposed on the favored limb as compared to the motion data acquired from the at least one other source to determine whether the potential physiological event is a reportable seizure event, and
in response to the motion data acquired from at least one of the accelerometer disposed on the favored limb or the at least one other source indicating a potential physiological event corresponding to an unclassified seizure type, provide an equal weighing factor to the motion data acquired from the accelerometer disposed on the favored limb and to the motion data acquired from the at least one other source to determine whether the potential physiological event is a reportable seizure event.

13. The method of claim 12, further comprising:
configuring the seizure detection system to acquire motion data exclusively from the favored limb.

14. The method of claim 12 wherein the at least one other source is at least one of a device providing an EEG signal, a device providing an ECG signal, a video device, a thermal imaging system, a motion detector, a depth sensor, an infrared laser device, or an accelerometer coupled to the subject's torso or head.

15. A method of detecting a seizure in a subject, the method comprising:
detecting the seizure with a seizure detection system, the seizure detection system acquiring motion data from a favored limb of the subject and from at least one other source, the favored limb being a limb of the subject that is associated with a better sensitivity and/or a better false positive rate in the detection of an anticipated seizure type as compared to the at least one other source of the subject when the seizure detection system is configured to detect said anticipated seizure type from motion data acquired from the at least one other source;
determining, via a processor, whether the detected seizure conforms with the anticipated seizure type; and
issuing, via the processor, an alert responsive to a determination to issue the alert of the detected seizure,
wherein when the detected seizure conforms with the anticipated seizure type, the determination to issue the alert is based on a first greater weight assigned to the motion data acquired from the favored limb, and
wherein when the detected seizure does not conform with the anticipated seizure type, the determination to issue the alert is based on a second greater weight assigned to the motion data acquired from the at least one other source and a lesser weight assigned to the motion data acquired from the favored limb, wherein the second greater weight is different from the first greater weight and the lesser weight is less than the first greater weight and the second greater weight.

16. The method of claim 15 wherein the anticipated seizure type is at least one of a hypermotor seizure or a seizure type associated with Sudden Unexplained Death in Epilepsy Patients ("SUDEP").

17. The method of claim 15 wherein the at least one other source is at least one of a device providing an EEG signal, a device providing an ECG signal, a video device, a thermal imaging system, a motion detector, a depth sensor, an infrared laser device, an accelerometer coupled to an un-favored limb of the subject, or an accelerometer coupled to a torso or a head of the subject.

* * * * *